United States Patent [19]
Walker

[11] Patent Number: 5,906,643
[45] Date of Patent: May 25, 1999

[54] STABILISED MOBILE BEARING KNEE

[76] Inventor: Peter Stanley Walker, 13 Pembroke Rd., Moor Park, Middlesex HA6 2HP, United Kingdom

[21] Appl. No.: 08/817,265
[22] PCT Filed: Jul. 27, 1995
[86] PCT No.: PCT/GB95/01781
    § 371 Date: Apr. 14, 1997
    § 102(e) Date: Apr. 14, 1997
[87] PCT Pub. No.: WO96/03097
    PCT Pub. Date: Feb. 8, 1996

[30] Foreign Application Priority Data

Jul. 28, 1994 [GB] United Kingdom .................. 9415180

[51] Int. Cl.$^6$ ....................................................... A61F 2/38
[52] U.S. Cl. .................................................................. 623/20
[58] Field of Search .................................. 623/16, 18, 20

[56] References Cited

U.S. PATENT DOCUMENTS

| | | | |
|---|---|---|---|
| 4,224,697 | 9/1980 | Murray et al. | 623/20 |
| 5,116,375 | 5/1992 | Hofmann | 623/20 |
| 5,314,483 | 5/1994 | Wehrli et al. | 623/20 |
| 5,330,534 | 7/1994 | Herrington et al. . | |
| 5,370,699 | 12/1994 | Hood et al. | 623/20 |
| 5,370,701 | 12/1994 | Finn | 623/20 |
| 5,387,240 | 2/1995 | Pottenger et al. | 623/20 |
| 5,395,401 | 3/1995 | Bahler | 623/20 |
| 5,609,639 | 3/1997 | Walker | 623/20 |
| 5,658,342 | 8/1997 | Draganich et al. | 623/20 |
| 5,683,468 | 11/1997 | Pappas | 623/20 |

FOREIGN PATENT DOCUMENTS

| | | |
|---|---|---|
| 0 381 352 A1 | 8/1990 | European Pat. Off. . |
| 0 510 299 A1 | 10/1992 | European Pat. Off. . |
| 0 627 203 A2 | 12/1994 | European Pat. Off. . |
| WO 94/26212 | 12/1994 | WIPO . |

Primary Examiner—Mickey Yu
Assistant Examiner—Bruce E. Snow
Attorney, Agent, or Firm—Burns, Doane, Swecker & Mathis LLP

[57] ABSTRACT

A prosthesis for total knee replacement (TKR) includes: a femoral component having a pair of condylar-bearing surfaces (10,12), a tibial component having a tibial platform (22) with an upstanding abutment (18) located between the condylar-bearing surfaces, and a meniscal component (15) interposed between the condylar-bearing surface and the tibial platform for sliding movement in the anterior-posterior (A-P) direction. The femoral component has an intercondylar projecting surface (20) adapted to contact the upstanding abutment at high degrees of flexion so as to influence the sliding movement of the meniscal component in a posterior direction.

12 Claims, 4 Drawing Sheets

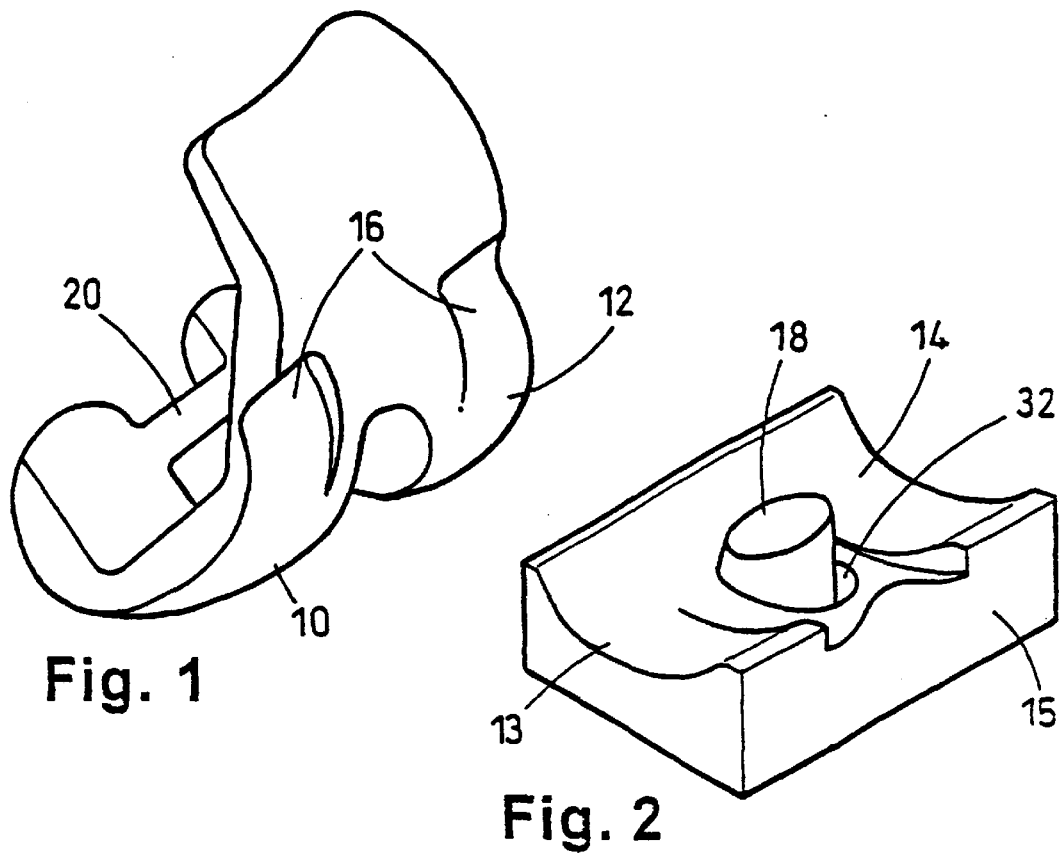
Fig. 1
Fig. 2
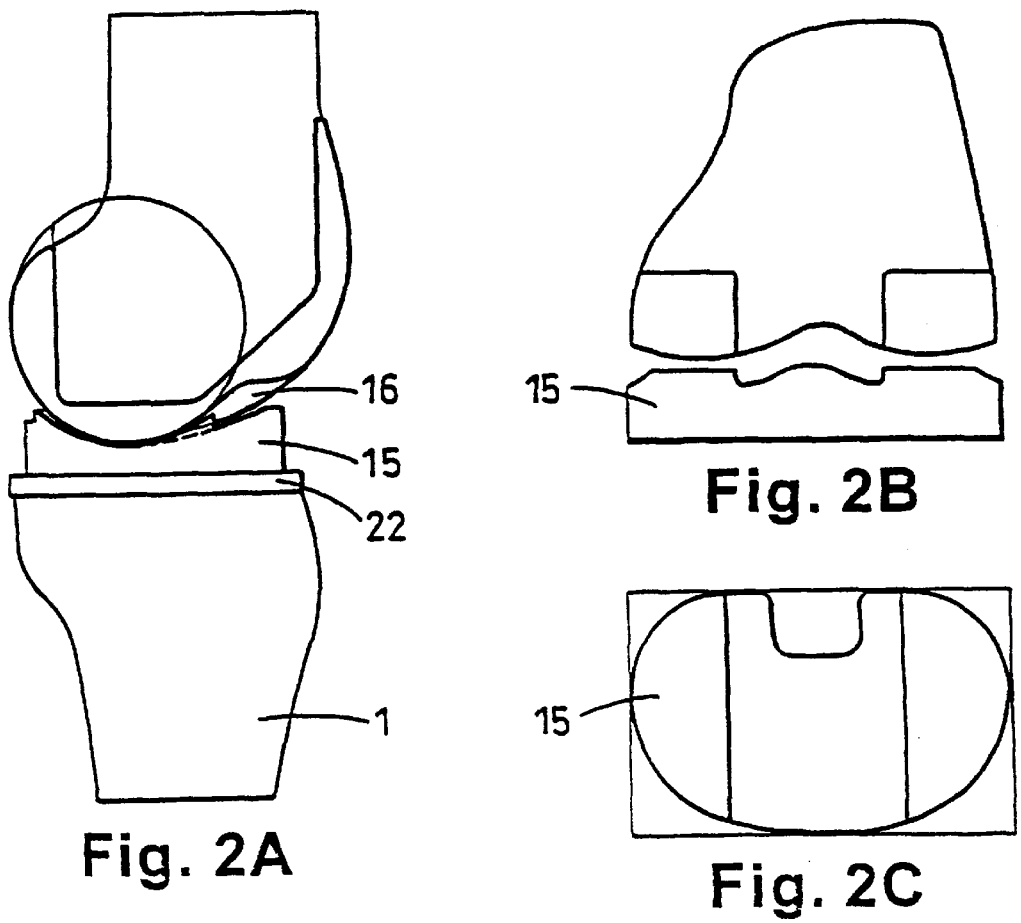
Fig. 2A
Fig. 2B
Fig. 2C

STABILISED MOBILE BEARING KNEE

BACKGROUND OF THE INVENTION

1. Field of the Invention

This invention relates to a total knee replacement prosthesis. Total knee replacement prostheses involve the surgical removal of the entire natural knee-bearing surfaces and their replacement with artificial femoral and tibial components. The femoral component includes condylar bearing surfaces which, to some extend, mimic the shape of the natural condyles.

2. Discussion of Related Art

The present invention relates to total knee replacement (TKR) prostheses of the three component type in which a floating meniscal component is interposed between the femoral and tibial components. The use of a meniscal component extends the range of movements that can be accommodated, including providing for a greater range of laxity of both sliding and rotational movement.

There are, however, several problems in designing a fully satisfactory TKR. One of these is to provide a high degree of flexion since, otherwise, the pre-operative range of flexion is not achieved and mobility is reduced. A high degree of flexion can be achieved by providing for roll back at maximum flexion. However, this is often achieved by providing for roll back at maximum flexion. However, this is often achieved at the risk of reduced stability. It is also important to achieve stability in extension, e.g. when the patient is standing. These requirements are difficult to achieve in a three component TKR.

SUMMARY

According to one aspect of the present invention there is provided a prosthesis for total knee replacement which comprises:

(a) a femoral component having a pair of condylar-bearing surfaces, (b) a tibial component having a tibial platform with an upstanding abutment located between the condylar-bearing surfaces, and (c) a meniscal component interposed between the condylar-bearing surface and the tibial platform for sliding movement in the anterior-posterior direction, said femoral component having an intercondylar projecting surface adapted to contact the upstanding abutment at high degrees of flexion so as to influence the sliding movement of the meniscal component in a posterior direction.

In one embodiment, the abutment may be a post extending upwardly through an aperture in the meniscal component and having a surface adapted to engage the intercondylar projecting surface at some point in its flexion.

The upstanding post or abutment may also serve to guide the plastic meniscal component in the A-P direction.

In one embodiment, the post may extend through an aperture or space between the condylar surfaces and engage the intercondylar projection only at high degrees of flexion, e.g. at degrees of flexion of at least 60 or 70°. The post or abutment may also engage with surfaces on the femoral component in extension so as to increase stability in extension but not engage with surfaces on the femoral component or intercondylar projection at degrees of flexion between extension and high degrees of flexion.

In another embodiment, the femoral component may have a substantially continuous surface constituting the intercondylar surface, e.g. in the form of a housing. Such a continuous surface may be in the form of a recess dividing the condylar bearing surfaces and the upstanding post may be accommodated in such recess. Again, however, the post and the intercondylar surface are preferably shaped and juxtaposed so that the post contacts the intercondylar surface only at high degrees of flexion and optionally also in extension. The reason for this is to avoid a situation where the joint is in danger of 'locking up' because of continuous contact between several surfaces. The Applicant has determined that additional stability is required essentially only where the joint is at high flexion, particularly where the prosthesis incorporates a highly conforming, congruent condylar component and meniscal component.

The intercondylar projection or surface may extend between the condyles and have a surface which, together with the surface of the post, has a camming action influencing the posterior movement of the meniscal component in high degrees of flexion.

BRIEF DESCRIPTION OF THE DRAWINGS

One embodiment of the invention will now be described with reference to the accompanying drawings, in which:

FIG. 1 shows a perspective view of the femoral component,

FIG. 2 is a similar perspective view of the meniscal component drawn rectangularly for simplicity and showing the guide post extending through the meniscal component from the tibial base plate (not shown), FIG. 2A is a side elevation of the assembled TKR with the tibial base plate fixed to a resected tibia, FIG. 2B is a front elevation of the femoral component about to be brought into contact with the meniscal component, FIG. 2C is a plan view of the meniscal component.

DETAILED DESCRIPTION OF THE INVENTION

Figure 3:
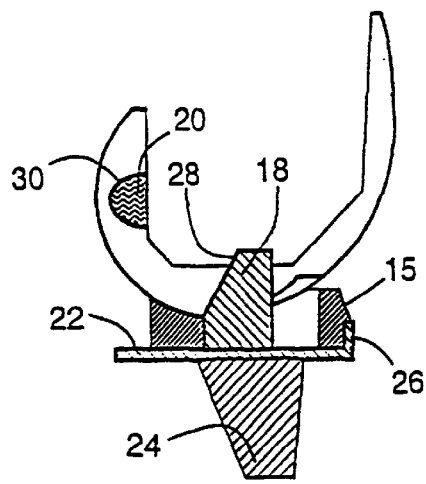
FIGS. 3, 4, 5, 6, 7 and 8 are sectional elevations showing the femoral component at various indicated angles of flexion.
Figure 4:
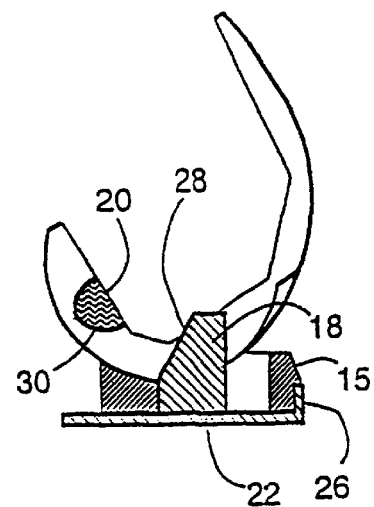
Figure 5:
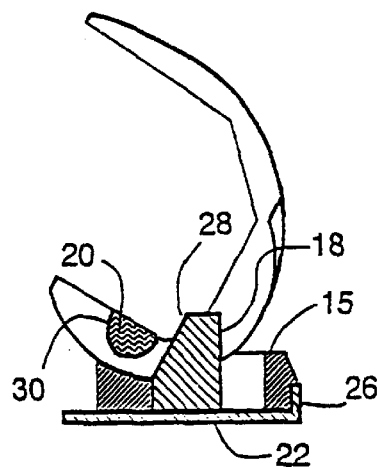
Figure 6:
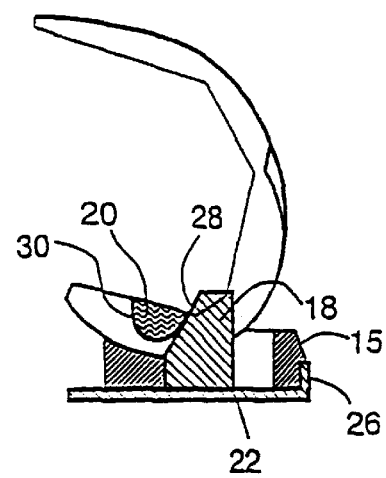

Referring to the drawings, the femoral component preferably has a high degree of conformity with corresponding bearing surfaces on the meniscal component. The femoral component may be substantially as described in our PCT Application No. PCT/GB94/01047 (WO 94/26212), and have a pair of condyles 10 and 12, which are shaped to correspond closely in saggittal planes with corresponding meniscal bearing-surfaces 13 and 14, formed in the upper surface of a meniscal component 15. The femoral component has cut-away portions 16 which extend the degree of flexion over which the condyles 10 and 12 are in close contact with the corresponding meniscal-bearing surfaces.

As shown diagrammatically in FIG. 2, a guide post 18 is attached to a tibial base plate as shown, e.g. in FIGS. 3 to 8, and extends through a hole or slot 32 in the meniscal component. This slot or hole is elongated in the anterior-posterior direction and is generally closed at both ends. The femoral component has an intercondylar guide surface 20 linking the two condyles 10 and 12. The interaction of the intercondylar projection 20 with the plastic guide post 18 is illustrated in FIGS. 3 to 8.

As can be seen in FIG. 3, the guide post 18 is secured to tibial base plate 22 which has a stud 24 for attachment to the resected tibia. Meniscal component 15 is trapped between the tibial base plate and the femoral component but, as will be described below, has a limited degree of freedom of movement. In the position shown in FIG. 3, the guide post 18 links the three components loosely together and provides, together with the anterior stop 26 on the tibial base plate, some stability in extension.

Plastic guide post 18 has a sloping surface 28 and intercondylar projection 20 has a curved cam-like surface 30. Consequently, as the femoral component begins to pivot on the meniscal component, the projection 20 moves closer to the sloping face 28 of the guide post. When a degree of flexion of about 75° is reached (FIG. 6), the intercondylar projection 20 touches the surface 28 of the plastic guide post 18.

Figure 7:
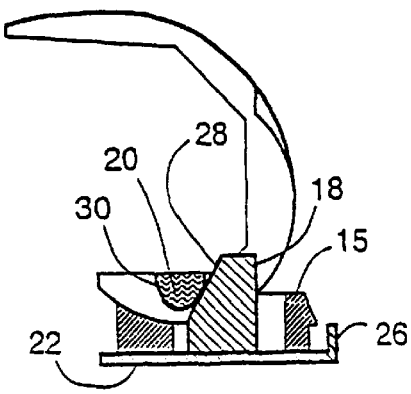

Because the surface of the condyles corresponds in close conformity with the meniscal-bearing surfaces 13 and 14, the effect of the projection 20 touching and sliding over the surface 28 is to cause the meniscal component to slide back on the tibial base plate (see FIG. 7). This movement has reached its maximum in FIG. 8 where the meniscal component has slid back until the end of the slot 32 through which the post extends abuts against the back surface 34 of the post. This abutment of the post with the end of the slot also prevents any tendency of the meniscal component to flip up from contact with the tibial base plate.

Figure 13:
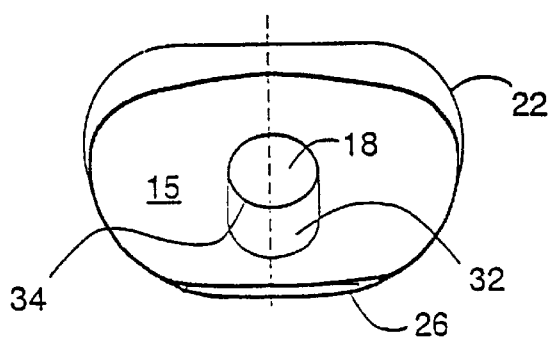
FIGS. 13 and 14 are plan views showing the sliding movement of the meniscal component or the tibial base plate.
Figure 14:
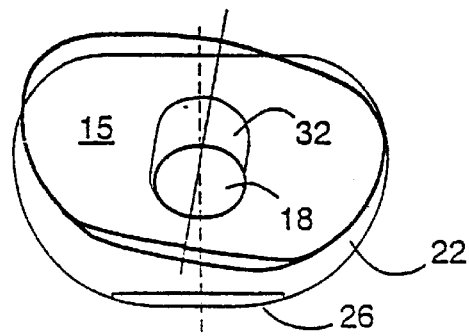
Figure 15:
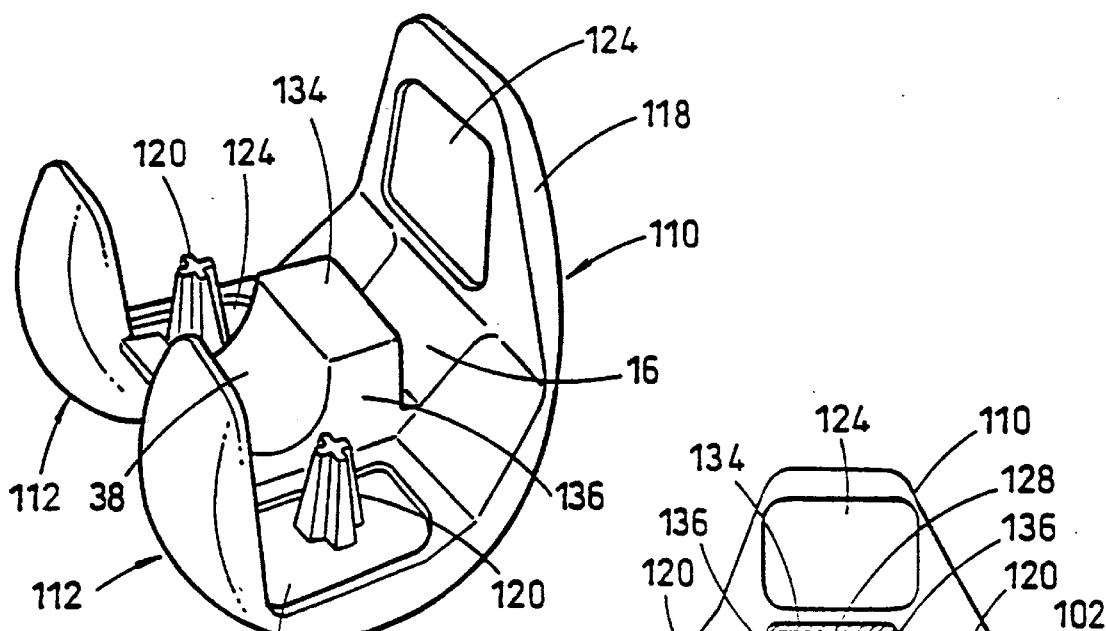
FIGS. 15 and 16 are perspective views of a second embodiment in accordance with the invention.
Figure 17:
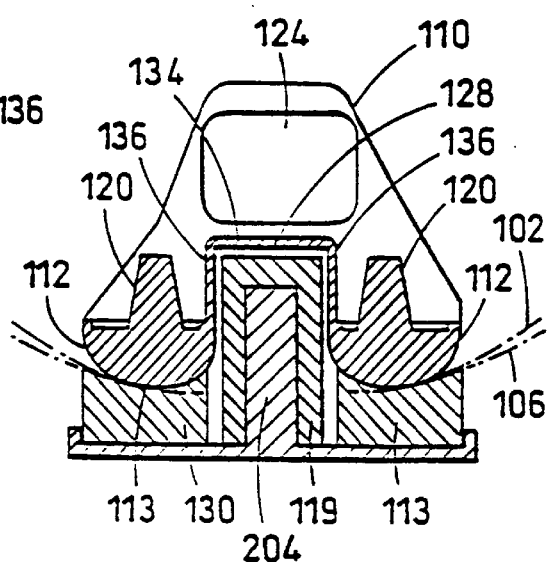
FIG. 17 is a lateral, cross-sectional view of the assembled prosthesis shown in FIGS. 15 and 16.

FIGS. 13 and 14 show the corresponding movement of the meniscal component on the tibial plate. In FIG. 14, the meniscal component 15 is at its maximum movement in the anterior direction and is in contact with the anterior stop 26. As can be seen, the slot 32 is elongated, thus giving a significant degree of freedom of movement to the meniscal component 15 in the A-P direction.

Figure 8:
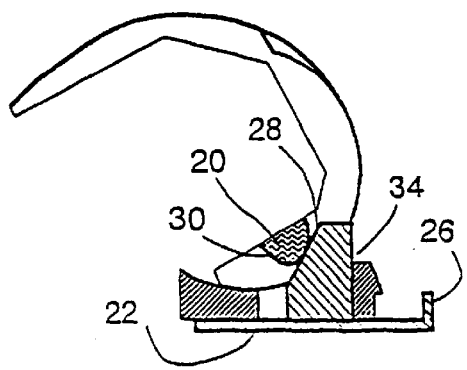
Figure 9:
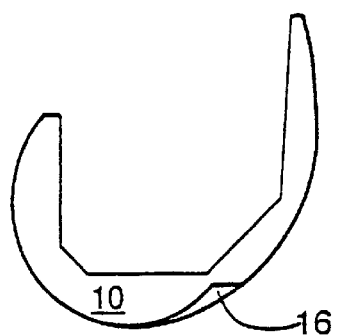
FIG. 9 is a side view of the femoral component.
Figure 10:
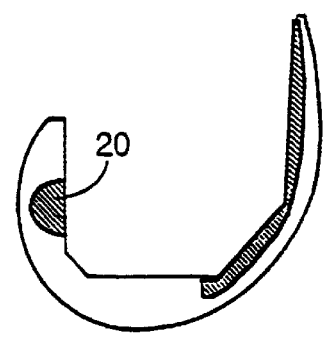
FIG. 10 is a similar side view, partly in section, showing the patella-bearing surfaces and the intercondylar guide surface.
Figure 11:
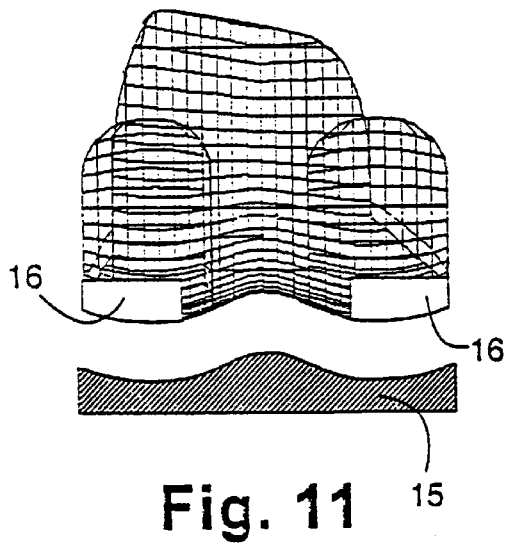
FIG. 11 is an anterior view of the femoral component and meniscal component, but not showing the post or abutment.

FIG. 14 shows the meniscal component in a position corresponding with FIG. 8, in which the meniscal component has abutted the anterior face 34 of the post 18. As can be seen from FIG. 14, the meniscal component 15 has a degree of rotational freedom of movement which is usually plus or minus 10–15°. This rotational freedom of movement provides the desired degree of laxity in the rotational dimension. Additional guides may be provided, e.g. on the tibial base plate, to assist the rotation of the meniscal component as it slides back. Because the guide post is non-rotationally secured to the tibial base plate, it provides a stable anchor point about which the meniscal component can be guided. Rotational movement of the meniscal component on the tibial base plate can be limited (e.g. to ±10–15°) by impingement on the post and/or engagement of the meniscal component with other guide surfaces on the tibial base plate.

Figure 12:
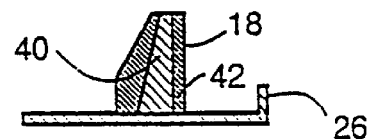
FIG. 12 is a view, partly in section, of the tibial base plate showing the guide post in detail.

As can be seen best in FIG. 12, the guide post is preferably formed from an internal metal post 40 which is sheathed with a plastic cap 42. This avoids the risk of metal to metal contact between the intercondylar guide surface 30 and the sloping face 28 of the guide post. Alternatively, the post 18 may be wholly of metal and the intercondylar guide may have a plastics surface. Suitable plastics materials for the sheath of the guide post and the meniscal component may be ultra-high molecular weight polyethylene.

FIGS. 15 to 18 show a second embodiment in which the femoral component has a lower surface which is continuous. The femoral component 110 is usually a metal casting or forging and includes a pair of condylar portions 112 having curved bearing surfaces 113 shaped to cooperate with corresponding bearing surfaces 121 of a plastics meniscal component 130. Pegs 120 serve to fix the femoral component into the resected femur. Recesses 124 are provided to receive bone cement. A patella track is provided on the anterior portion 118. Between the condylar portions 112 is located a box-like structure 134 having a downwardly open mouth for receiving an abutment or peg 119 (see FIGS. 16–18).

Figure 16:
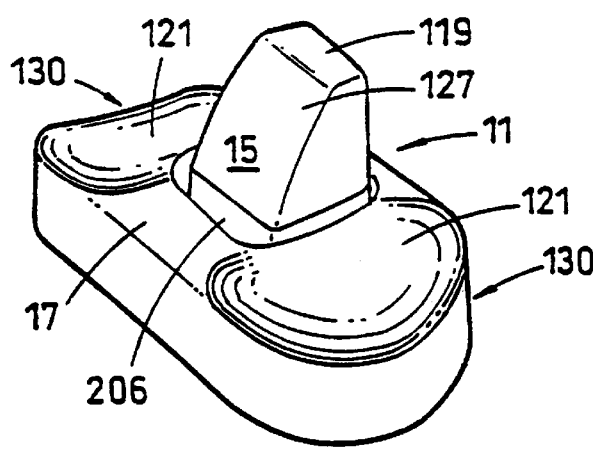
Figure 18:
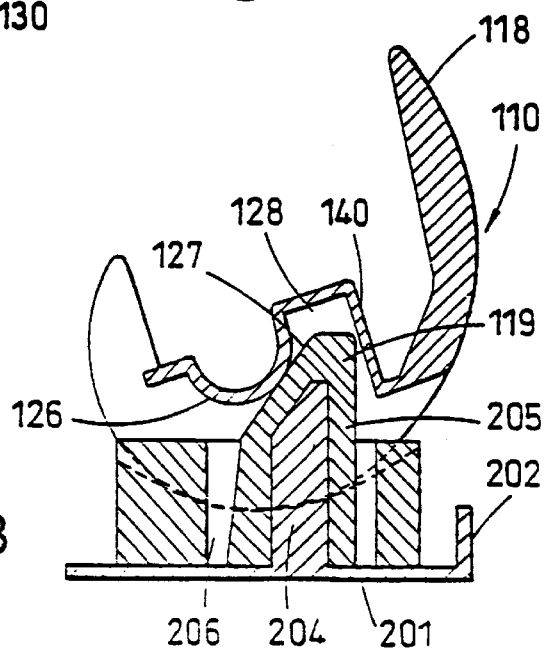
FIG. 18 is a cross-sectional view of the prosthesis shown in FIG. 17 taken in the anterior-posterior direction.

Peg 119 is fixed to a metal tibial base plate 201 having an anterior rim stop 202. The peg 119 comprises a metal core 204 having a plastic sheath 205 projecting through a slot 206 in the meniscal component 130. As can be seen in FIGS. 16 and 18, the peg 119 has a sloping posterior face 127 which engages on a rounded face 126 in the interior of the box structure 134.

When the prosthesis is in its extended position the tip of the peg 119 is located within a recess 128 in the box-like structure. In this condition, the joint is stabilised in an A-P direction by interaction of the anterior face of the peg and the anterior wall 140 of the box-like structure. Also, the prosthesis is stabilised laterally by the interaction between the slide faces of the peg with the lateral walls of the box-like structure 134.

When the femoral component undergoes flexion, the curved interior surface 126 engages the sloping face 127 of the peg which causes both the femoral component and the meniscal component to roll back. Slot 206 limits the degree of posterior sliding movement of the meniscal component.

The base plate 201 may be fitted with a downward peg or pegs, e.g. similar to peg 24 in FIG. 3, to aid fixture to a resected tibia.

I claim:

1. A prosthesis for total knee replacement (TKR) which comprises:

(a) a femoral component having a pair of condylar bearing surfaces, (b) a tibial component having a tibial platform and an upstanding stabilizing post fixed to the platform and located between the condylar-bearing surfaces, and (c) a meniscal component interposed between the condylar bearing surface and the tibial platform for sliding movement on the tibial platform in the anterior-posterior (A-P) direction, said meniscal component having an aperture therethrough and said post extending through said aperture, said femoral component having an intercondylar projecting surface which bridges said condylar surfaces and is adapted to contact the post at high degrees of flexion so as to influence the sliding movement of the meniscal component in a posterior direction, and wherein the aperture in the meniscal component is elongated in the A-P direction and cooperates with said post for guiding sliding movement of the meniscal component in the A-P direction, wherein the stabilizing post is spaced from the intercondylar projecting surface at low flexion and contacts said surface only at high degrees of flexion.

2. A prosthesis as claimed in claim 1, wherein the meniscal component is capable of rotation about said post.

3. A prosthesis as claimed in claim 2, wherein the tibial platform additionally includes one or more stops limiting A-P movement and/or rotational movement of the meniscal component.

4. A prosthesis as claimed in claim 1, wherein the stabilizing post has a plastic surface.

5. The prosthesis as claimed in claim 1, wherein the stabilizing post only contacts the intercondylar projecting surface at flexion of about 75° or greater.

6. A prosthesis as claimed in claim 1, wherein the femoral component has an anterior surface providing a patella bearing surface and the intercondylar projecting surface only bridges the condyles at a point remote from the patella bearing surface.

7. A prosthesis as claimed in claim 1, wherein the intercondylar projecting surface comprises a housing located between the condyles and into which the stabilizing post projects.

8. A prosthesis for total knee replacement (TKR) which comprises:

a femoral component having a pair of condylar bearing surfaces;

a tibial component having a tibial platform and an upstanding stabilizing post fixed to the platform and located between the condylar-bearing surfaces; and a meniscal component interposed between the condylar bearing surface and the tibial platform for sliding movement on the tibial platform in the anterior-posterior (A-P) direction, said meniscal component having an aperture therethrough and said post extending through said aperture;

said femoral component having an intercondylar projecting means which bridges said condylar surfaces at one end thereof for contacting the post only at high degrees of flexion so as to initiate a sliding movement of the meniscal component in a posterior direction;

wherein the aperture in the meniscal component is elongated in the A-P direction and cooperates with said post for guiding sliding movement of the meniscal component in the A-P direction.

9. The prosthesis as claimed in claim 8, wherein the high degree of flexion is about 75°.

10. A prosthesis as claimed in claim 8, wherein the meniscal component is capable of rotation about said post.

11. A prosthesis as claimed in claim 10, wherein the tibial platform additionally includes one or more stops limiting A-P movement and/or rotational movement of the meniscal component.

12. A prosthesis as claimed in claim 8, wherein the stabilizing post has a plastic surface.

* * * * *